(12) United States Patent
Yukimoto et al.

(10) Patent No.: US 9,386,761 B2
(45) Date of Patent: Jul. 12, 2016

(54) ENVIRONMENTALLY ACTIVE CONCRETE (75) Inventors: Takaki Yukimoto, Tokyo (JP); Yasuhiro Kaneko, Tokyo (JP); Seishi Tokunaga, Tokyo (JP); Hirokazu Nishimura, Tokyo (JP); Tatsuru Tabohashi, Tokyo (JP); Masaki Kobayashi, Tokyo (JP); Kazuhiro Sato, Tokyo (JP); Chizuru Tara, Tokyo (JP)

(73) Assignee: Nikken Kogaku Co., LTD, Tokyo (JP)

( * ) Notice: Subject to any disclaimer, the term of this patent is extended or adjusted under 35 U.S.C. 154(b) by 548 days.

(21) Appl. No.: 13/520,220

(22) PCT Filed: Oct. 19, 2010

(86) PCT No.: PCT/JP2010/068798
§ 371 (c)(1),
(2), (4) Date: Jul. 2, 2012

(87) PCT Pub. No.: WO2011/086744
PCT Pub. Date: Jul. 21, 2011

(65) Prior Publication Data
US 2013/0023581 A1    Jan. 24, 2013

(30) Foreign Application Priority Data

Jan. 15, 2010 (JP) ................................. 2010-007456

(51) Int. Cl.
| | |
|---|---|
| *E02B 3/12* | (2006.01) |
| *A01K 61/00* | (2006.01) |
| *A01N 25/00* | (2006.01) |
| *A01N 37/50* | (2006.01) |
| *C04B 14/00* | (2006.01) |
| *C04B 24/12* | (2006.01) |
| *C04B 24/14* | (2006.01) |
| *C04B 28/02* | (2006.01) |
| *C04B 103/30* | (2006.01) |
| *C04B 111/00* | (2006.01) |
| *C04B 111/72* | (2006.01) |
| *C04B 111/74* | (2006.01) |

(52) U.S. Cl.
CPC ............ *A01K 61/006* (2013.01); *A01N 25/002* (2013.01); *A01N 37/50* (2013.01); *C04B 14/00* (2013.01); *C04B 24/123* (2013.01); *C04B 24/14* (2013.01); *C04B 28/02* (2013.01); *E02B 3/129* (2013.01); *C04B 2103/30* (2013.01); *C04B 2111/00758* (2013.01); *C04B 2111/72* (2013.01); *C04B 2111/74* (2013.01)

(58) Field of Classification Search
CPC ...... A01K 61/006; C04B 24/14; C04B 28/02; C04B 14/00; C04B 24/123; C04B 2111/72; C04B 2111/74; C04B 2103/30; E02B 3/129; A01N 25/002; A01N 37/50
USPC ................................................ 514/44 R, 565
See application file for complete search history.

(56) References Cited

FOREIGN PATENT DOCUMENTS

| JP | 46-14848 | 5/1971 |
|---|---|---|
| JP | 62-7422 | 2/1987 |
| JP | 10-001352 | 1/1998 |
| JP | 2000-336630 | 12/2000 |
| JP | 2005-348717 | 12/2005 |
| JP | 2006-348572 | 12/2006 |
| JP | 2007-181457 | 7/2007 |
| JP | 2007-215532 | 8/2007 |
| JP | 2008-295441 | 12/2008 |
| JP | 2009-171932 | 8/2009 |

OTHER PUBLICATIONS

JP 10-001352 machine generated translation.*
JP 2009-171932 machine generated translation.*

* cited by examiner

*Primary Examiner* — John Pak
*Assistant Examiner* — Nathan W Schlientz
(74) *Attorney, Agent, or Firm* — Fattibene and Fattibene LLC; Paul A. Fattibene (57) ABSTRACT

In order to reduce the amount of an organism attractant substance remaining inside concrete that tends be used wastefully and also to allow the organism attractant substance to effectively flow out gradually in a long period of time, an environmentally active, preserving and repairing-use concrete block is provided in which the air content and flowability of the concrete are increased, and the congregating and growing effects for fishes and shellfishes and the adhering and growing effects for algae are maintained so that a high attractant effect by odor of the organism attractant substance is obtained.

An environmentally active preserving and repairing-use concrete block is provided with at least three or more legs, and in this structure the environmentally active preserving and repairing-use concrete block is formed by using an environmentally active preserving and repairing-use concrete having high air content and high flowability formed by kneading an organism attractant substance having a specific odor therein.

6 Claims, 6 Drawing Sheets

ENVIRONMENTALLY ACTIVE CONCRETE

FIELD OF THE INVENTION

The present invention relates to an environmentally active concrete, and in particular concerns such an environmentally active concrete for use in an environment activation-use block made of concrete to be used for revetments for fishing harbor, harbors, coasts, rivers, etc., or for artificial fish reefs to be sunk onto the sea bed, etc.

DESCRIPTION OF THE RELATED ART

Conventionally, it has been known that in fishing harbor, harbors, coasts, rivers, etc., in order to block oncoming waves from the open sea or the like to maintain a calm water surface, wave-absorbing blocks are placed and arranged near the coast to form a coastal bank (for example, see Japanese Patent Application Laid-Open No. 2000-336630).

As the wave-absorbing block described in the Japanese Patent Application Laid-Open No. 2000-336630, a concrete block having at least three or more legs is used.

In this case, as the blocks to be used for revetments for fishing harbor, coasts, rivers, etc., or for artificial fish reefs to be sunk onto the sea bed, etc., those blocks that are superior in effects for allowing organisms to congregate, adhere and grow thereon, in particular, effects for allowing fish to congregate and grow around them are required.

In order to obtain the congregating, adhering and growing effects for organisms, the following methods have been known: the concrete surface is roughened or formed into a fine structure so as to allow sea weeds to adhere thereto (Japanese Patent Application Laid-Open No. 2007-215532), an amino acid is applied onto the surface of the concrete block (Japanese Patent Application Laid-Open No. 2000-336630), an amino acid is kneaded into concrete upon producing a concrete block (Japanese Patent Application Laid-Open No. 2008-295441), and a waste fluid of distilled liquor is kneaded into concrete upon producing a concrete block (Japanese Patent Application Laid-Open No. 2005-348717, Japanese Patent Application Laid-Open No. 2007-181457 and Japanese Patent Application Laid-Open No. 2009-171932); thus, concrete blocks having the effects for allowing organisms to congregate, adhere and grow thereon are obtained.

As described above, the method for roughening the surface of a concrete block or forming a fine structure on the surface thereon and the method for applying an organism attractant thereto, or the method for kneading an organism attractant substance in a concrete block are advantageous in that a large facility and a time-consuming task are not required.

SUMMARY OF THE INVENTION

However, the concrete block described in Japanese Patent Application Laid-Open No. 2007-215532 is used only for accelerating adhesion of organisms thereto, and no growing effect can be expected, and although indirect effects for generated sea weeds can be expected, the congregating and growing effects for fishes are hardly obtained in principle. The structure of a concrete block having a surface to which an organism attractant substance is applied, as described in Japanese Patent Application Laid-Open No. 2000-336630, is expected to exert congregating, adhering and growing effects for organisms by allowing the organism attractant substance to flow into the environment; however, in the case when sunk into water, since the surface thereof is washed away by streams and waves by the river or the like, with the result that the organism attractant substance is soon separated off and washed away, failing to maintain it for a long period of time. The resulting problem is that it is not possible to maintain the congregating and growing effects for gathering fishes and shellfishes at one place and the adhering and growing effects for sea weeds, for a long period of time.

On the other hand, in the case of a concrete block in which an organism attractant substance is kneaded, as shown by a concrete block described in Japanese Patent Application Laid-Open No. 10-1352, since the kneaded organism attractant substance is allowed to gradually flow out of the concrete block, the congregating, adhering and growing effects for organisms can be maintained for a long period of time. However, in Japanese Patent Application Laid-Open No. 10-1352, since the amount of a remarkably effective substance for use in attracting organisms is so little that, although slight adhesion of sea weeds and shellfishes can be observed, attracted fishes or the like are not observed. Moreover, a solid-state material described in Japanese Patent Application Laid-Open No. 2005-348717, Japanese Patent Application Laid-Open No. 2007-181457 and Japanese Patent Application Laid-Open No. 2009-171932 uses a waste liquid of distilled liquor as its organism attractant substance, with the result that the waste liquid of distilled liquor is not blended at a high concentration and that even if it is effective as the organism attractant substance, it forms a deterrent contained therein from the viewpoint of maintaining the strength of concrete.

Moreover, in the case of these kneaded-type concrete blocks, since the amount of the organism attractant substance to flow into water is small, and since some of the substance is enclosed into the concrete block, as it is, without flowing out, causing most of the substance to be used wastefully.

In order to solve the above-mentioned problems, an object of the present invention is to provide an environmentally active concrete and an environment activation-use block having congregating, adhering and growing effects for organisms, especially, congregating and growing effects for fishes.

Requirements for the environmentally active concrete composition that provides the congregating, adhering and growing effects for organisms, in particular, the congregating and growing effects for fishes, are first to allow a large amount of a remarkably effective organism attractant substance to be kneaded in the composition, second to allow the composition to have, for example, such a fine structure that the substance is allowed to effectively flow into water, third to allow the composition to have a sufficient strength required for forming an environmentally active concrete, and fourth to provide such a structure as to prevent the environmentally active concrete block obtained by the composition from being left inside the concrete.

With respect to the kneaded-type concrete block, its effect is exerted by allowing much organism attractant substance held in the concrete to be gradually released into the environment; however, in principle, the amount of flow is limited, and it is inevitable to select a remarkably effective organism attractant substance and to blend the substance in the concrete at a high concentration.

Although not particularly limited, examples of the organism attractant substance include: amino acid, alanine, arginine, asparagine, asparagic acid, cystine, cystain, glutamine, glutamic acid, glycine, histidine, isoleucine, leucine, lysine, methionine, phenylalanine, proline, serine, threonine, tryptophan, tyrosine, valine, etc., and as the nucleic acid, examples thereof include: inosine, guanine, adenosine, uridine, thymidine, etc.

The modes of these amino acid and nucleic acid are not particularly limited, and a pure simple substance or a mixture thereof may be used, or the amino acid or nucleic acid may be contained in a liquid, such as a fermentation waste. Moreover, a polymer containing an amino acid and a nucleic acid, such as protein, peptide, DNA, RNA, etc., may also be used; however, selection of the organism attractant substance needs to be made in such a degree as not to give influences to the effective flow thereof into the environment and the strength of concrete to be formed, as will be described later.

Moreover, the more the added amount of these amino acid and nucleic acid to the environment activation-use block composition, the better for the purpose of flowing out to the environment, as described earlier, and the added amount is set to 2% or more, preferably, to 3% or more relative to cement weight so as to achieve the effects of the present invention.

Furthermore, in order to form a block by using the environment activation-use block composition of the present invention, other additives may be added thereto without causing any problems. As such additives, an AE agent and a water-reducing agent are proposed.

The present invention has paid attention to a basic amino acid, in particular, arginine, as the remarkably effective organism attractant substance. As described in Non-Patent Literature 7 with respect to the effects of the amino acid for fishes, the amino acid improves the sensitivity of the sensory organ of fishes.

The concrete composition in which the basic amino acid is kneaded is, for example, described in Japanese Patent Application Laid-Open No. 2008-295441, and after examinations about the flowing out of these amino acids, it is clarified by the functional examinations that the compounding ratio of 3% or more relative to cement weight allows arginine to significantly flow out.

Moreover, as generally described in Japanese Patent Application Laid-Open No. 10-1352 and Japanese Patent Application Laid-Open No. 2007-181457, the attractant substance having a high compounding ratio causes a problem of failing to provide a sufficient strength to the concrete and subsequently failing to obtain a structural body.

The environment activation-use block composition in accordance with the present invention clearly indicates that, even when the arginine is added at a high compounding ratio, a sufficient strength required for obtaining the block structural body can be obtained, and that the resulting structural body has a specific gravity lower than that of concrete having no added compound. This indicates that the concrete composition containing arginine is porous and that the corresponding substance is easily allowed to flow in water.

The following description will discuss the results of submerging tests of the above-mentioned concrete composition. The submerging tests were carried out at two points in sea water and in river water, that is, experimental sites of a southern point of the Osaka Bay and a river in Yamaguchi Prefecture. Observations in two months after having been submerged indicated that in the sea water, the generation of algae was significantly observed on the arginine-kneaded concrete, with fishes congregating therearound. Moreover, in the submerging test in the river, bite marks by sweetfish were observed and eels that were growing within the block were observed on the arginine-kneaded concrete.

The following description will discuss the environment activation-use block molded by using the aforementioned environment activation-use block composition. The environment activation-use block described in Claim 5 is formed with three or more legs, and since the surface of each of the legs is made in contact with water, the surface area of the concrete block to be made in contact with water is maintained as a large area. Simultaneously, since it is formed by a porous concrete, a larger surface area to be made in contact with water can be maintained, and the inside of the concrete block is allowed to easily absorb water, and since the organism attractant substance absorbed and contained inside thereof is gradually ooze from the surface through the water thus absorbed, it becomes possible to increase the amount of the organism attractant substance to ooze into water from the entire concrete can be increased. Moreover, by providing a number of legs so as to maintain a large surface area, the thickness of the concrete block itself can be made thinner as a whole, thereby allowing the organism attractant substance to be efficiently flow out into the environment.

In the invention described in Claim 5, the above-mentioned legs form an environment activation-use block having at least three or more legs.

With this arrangement, since the respective legs are prepared to form the structure, the surface area of the concrete block that is made in contact with water is increased so that the amount of the organism attractant substance that oozes into water from the concrete surface can be increased.

The invention described in Claim 6 provides an environmentally active, preserving and repairing-use block in which the legs have plane portions, each prepared between a plurality of ridge line portions that are formed along the length direction of the leg, so as to be shaped into a pillar with polygonal surfaces.

With this structure, since each leg is shaped into a pillar with polygonal surfaces, the surface area of the concrete block to be made in contact with water is further increased so that the amount of organism attractant substance to ooze into water from the concrete surface is further increased.

The invention described in Claim 7 provides a method for congregating, adhering and growing organisms by using the concrete or the environmentally active, preserving and repairing-use block described in any one of Claims 1 to 6.

With this method, it becomes possible to congregate, adhere and grow organisms by using the environmentally active, preserving and repairing-use block described in any one of Claims 1 to 6.

The invention described in Claim 8 makes it possible to congregate, adhere and grow fishes by using the method described in Claim 7.

The present invention mainly provides an environmentally active concrete and an environment activation-use block that are superior in congregating, adhering and growing effects for organisms, in particular, congregating and growing effects for fishes.

As described in Claims 1, 2, 3 and 4, by blending a remarkably effective organism attractant substance to an environmental active concrete at a high compounding ratio, it becomes possible to allow the substance to effectively flow out from the block.

Moreover, as described in Claims 3 and 4, by adding arginine at a high concentration as the organism attractant substance, a porous concrete can be obtained without causing a reduction in the strength of the concrete. With this arrangement, the amount of the organism attractant substance to flow out into the environment can be increased, making it possible to obtain an environmentally active concrete that is superior in congregating, adhering and growing effects for organisms, in particular, in congregating and growing effects for fishes.

As described in Claim 5, the present invention is designed to maintain a large surface area of concrete that is made in contact with water and allow the organism attractant substance kneaded in the concrete to gradually ooze from the concrete surface in an appropriate amount portion by portion; therefore, the organism attractant substance is allowed to gradually flow effectively for a long period of time so that the congregating and growing effects for fishes and shellfishes and the adhering and growing effects for algae can be maintained for a long period of time. Moreover, since the thickness of a concrete block itself can be made thinner as a whole, the organism attractant substance is allowed to flow into the environment effectively.

As described in Claim 6 in the present invention, in the case when each of legs is formed into a pillar with polygonal surfaces, the amount of the organism attractant substance to ooze into water from the concrete surface can be further increased so that the congregating and growing effects for fishes and shellfishes and the adhering and growing effects for algae can be maintained for a longer period of time.

As described in Claims 7 and 8, the present invention makes it possible to congregate, adhere and grow organisms, such as fishes and shellfishes more effectively.

DETAILED DESCRIPTION OF THE PREFERRED EMBODIMENTS in order to achieve purposes of reducing the amount of an organism attractant substance that remains inside a concrete and is used wastefully and of allowing the organism attractant substance to gradually flow out for a long period of time to form a structure having congregating and growing effects for fishes and shellfishes as well as maintaining adhering and growing effects for algae for a long period of time, the present invention provides an environment activation-use block having at least three legs, that is formed with a porous concrete, with an organism attractant substance being kneaded therein.

Referring to attached Figs., the following description will discuss preferred embodiments of an environmentally active concrete and an environment activation-use block of the present invention.

FIGS. 1 to 6 show environment activation-use blocks to which the present invention is applied, by exemplifying a wave-absorbing block. In these Figs., a wave-absorbing block 1 is a concrete block having four legs 2a, 2b, 2c and 2d, each having the same shape, and this is integrally molded by pouring concrete, for example, into a frame work (not shown). Moreover, at the time of molding, the respective legs 2a, 2b, 2c and 2d are bonded to one another through the respective base end portions 3a, with axial lines 4 of the respective legs 2a, 2b, 2c and 2d being made coincident with the center O (center of gravity) of the wave-absorbing block 1, so that the respective four legs 2a, 2b, 2c and 2d are formed in such a manner as to be radially extended, each having an interval of virtually 120° from the center O.

Figure 1:
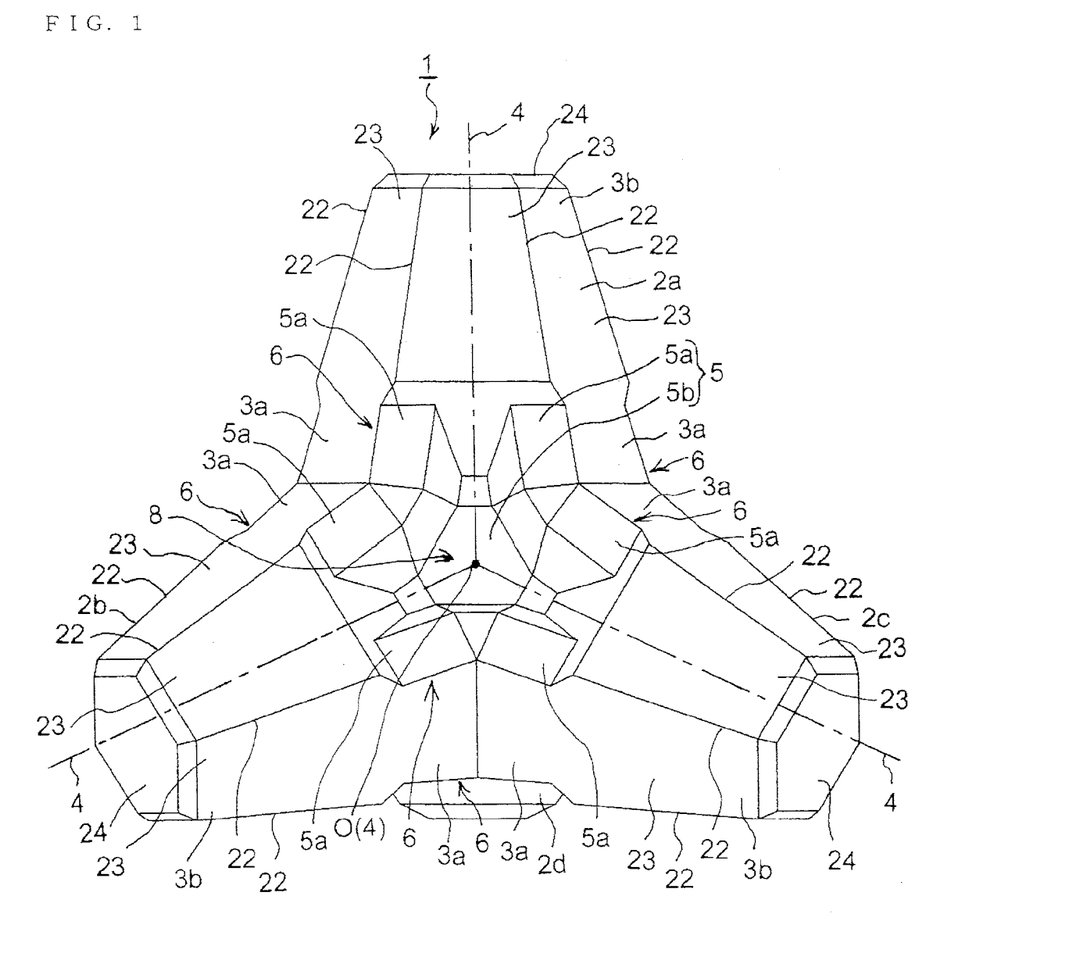
FIG. 1 is a front view showing a wave-absorbing block as one embodiment of the present invention.
Figure 2:
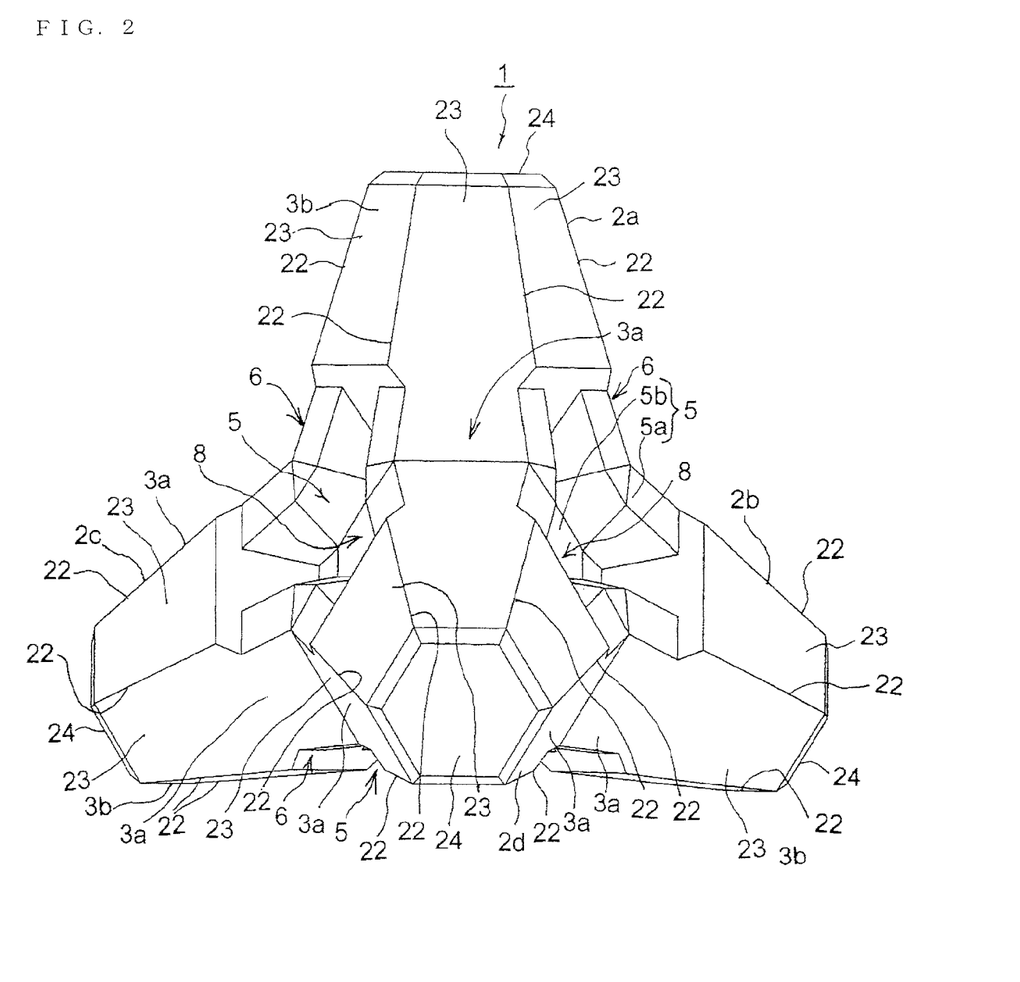
FIG. 2 is a back face view of the wave-absorbing block.
Figure 3:
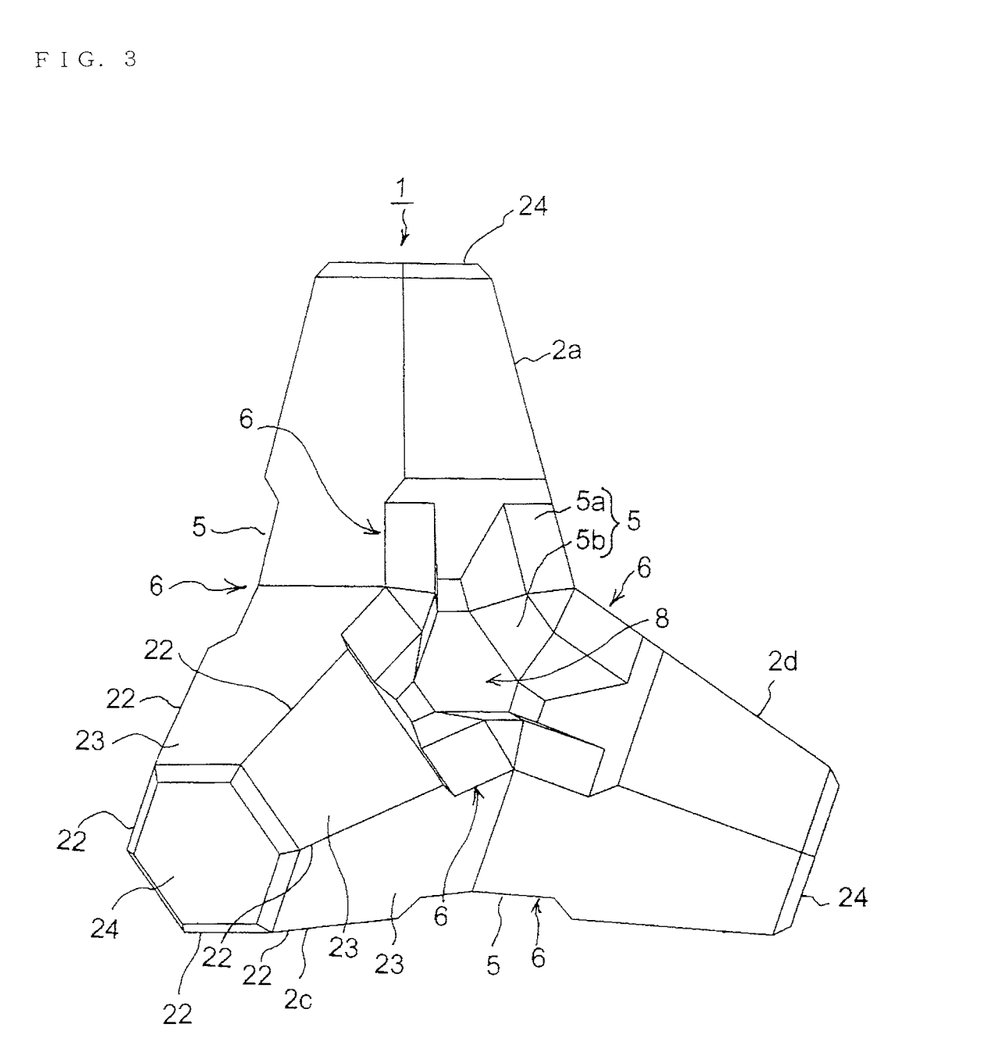
FIG. 3 is a right side view of the wave-absorbing block.
Figure 4:
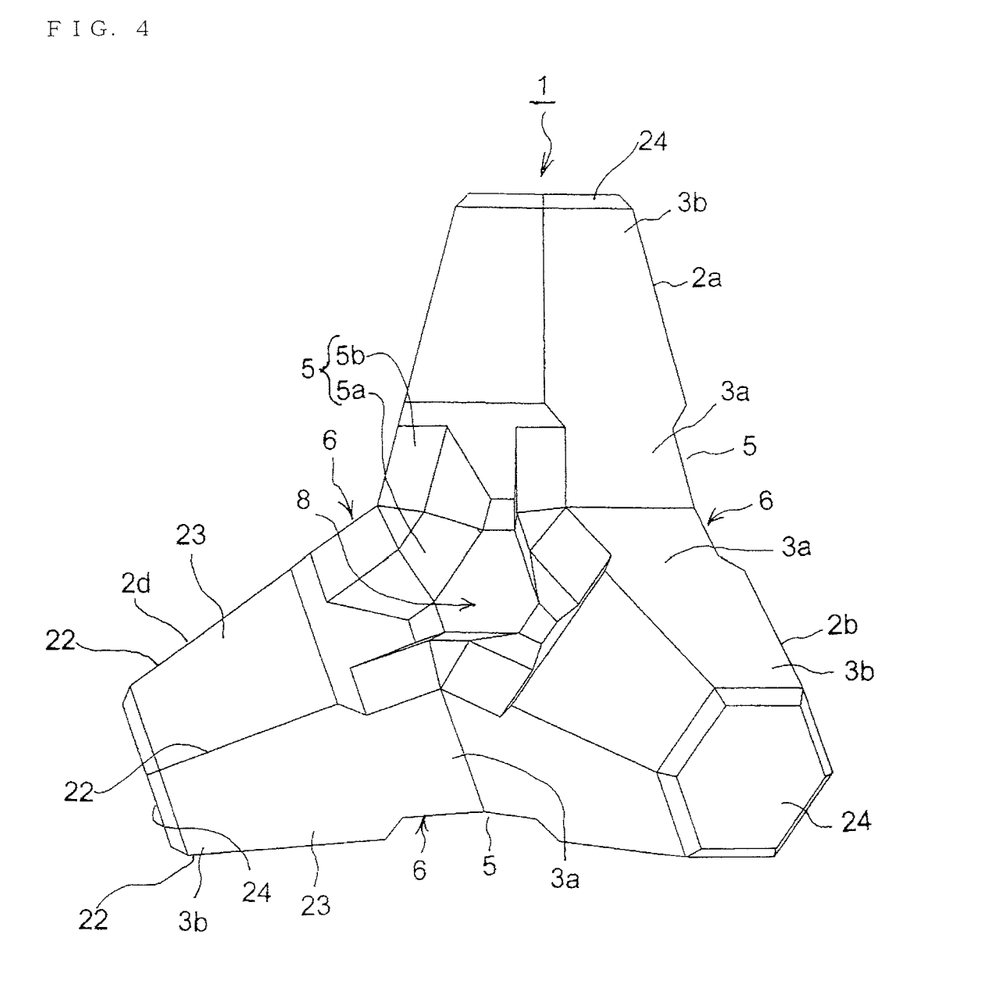
FIG. 4 is a left side view of the wave-absorbing block.
Figure 5:
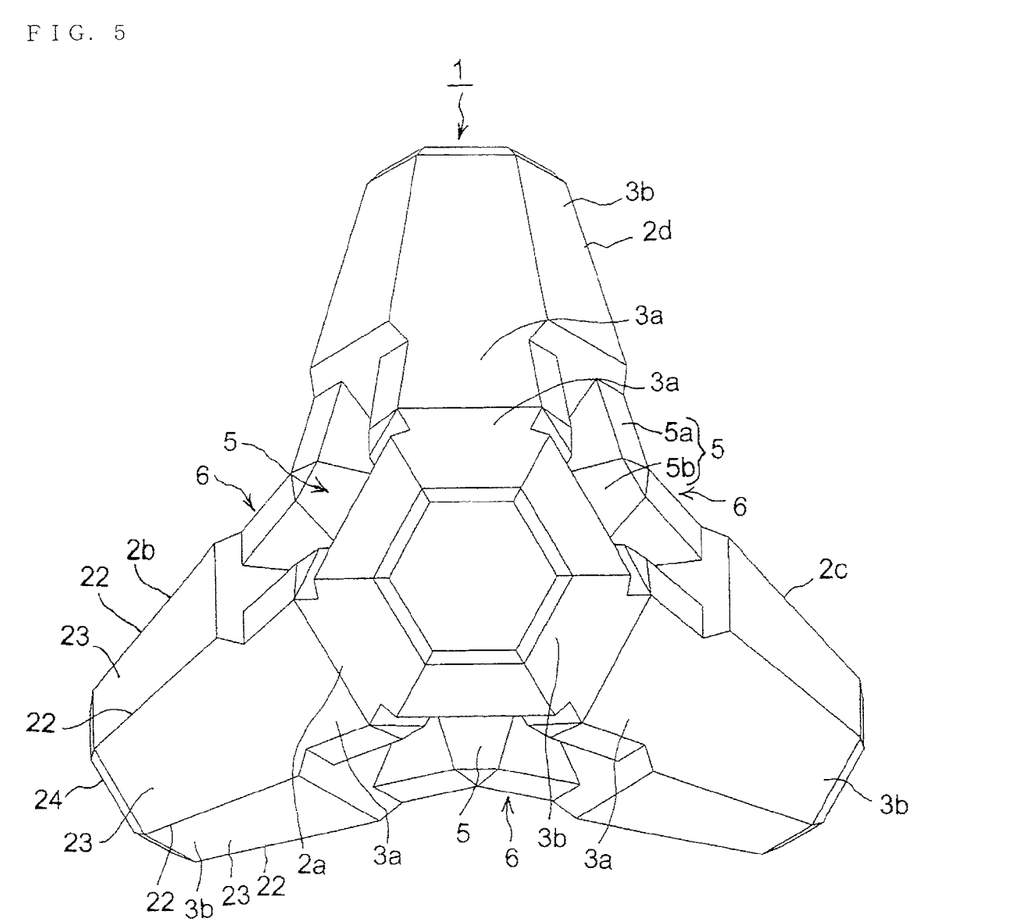
FIG. 5 is a plan view of the wave-absorbing block.
Figure 6:
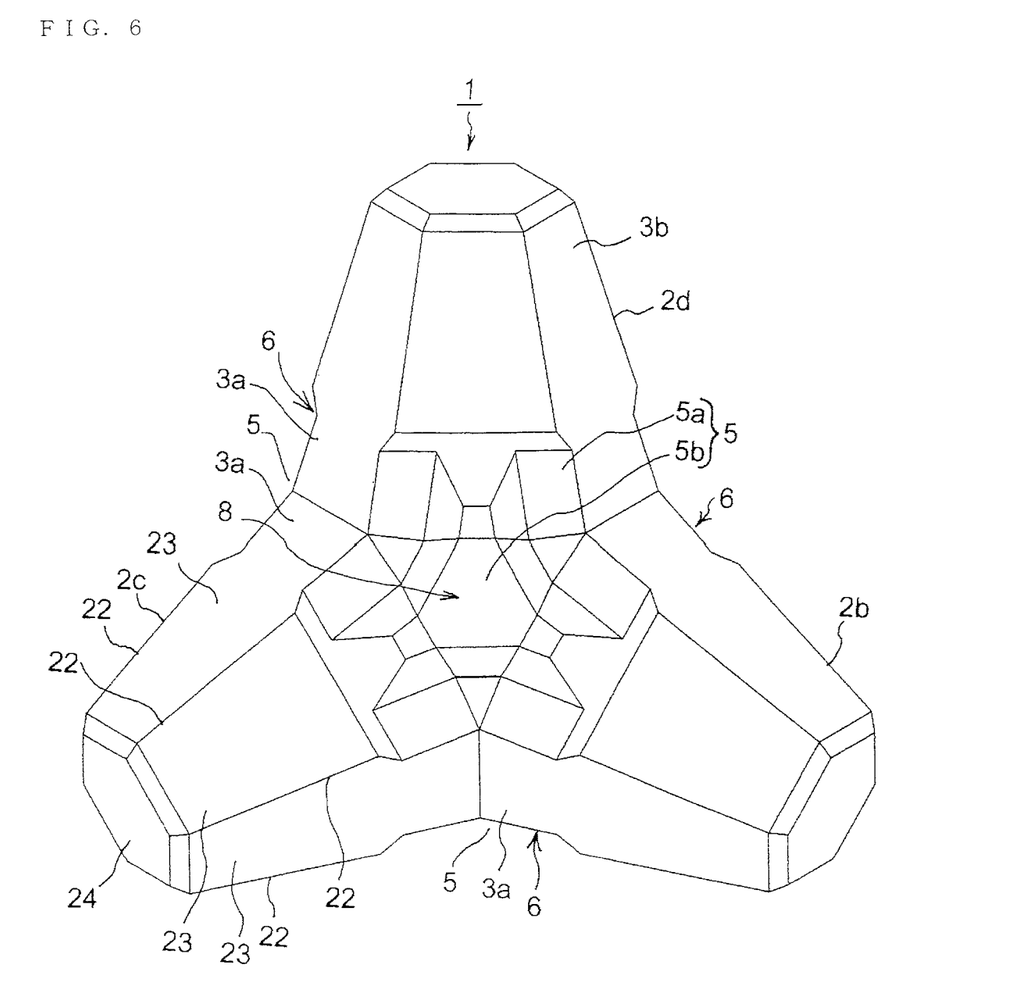
FIG. 6 is a bottom face view of the wave-absorbing block.

Additionally, in this molding process, upon kneading a standard kneading matter (hereinafter, referred to as "raw concrete") made from, for example, sand, cement and water, an organism, attractant substance, typically represented by an amino acid and a nucleic acid, is added to the raw concrete at a ratio of 3% to 7% or more relative to the entire ratio of the raw concrete, and the raw concrete in which the organism attractant substance has been kneaded is poured into the frame work to be solidified therein and molded into a predetermined shape.

As described earlier, in the case of the raw concrete in which the organism attractant substance, typically represented by an amino acid and a nucleic acid, has been kneaded, especially in the case of specifically selected amino acid and nucleic acid, the viscosity of the raw concrete is weakened for a short period of time until the raw concrete has been solidified. With this arrangement, the raw concrete is allowed to easily enter each of the corners of the frame work so that the molding process is easily carried out. On the other hand, after having been solidified, porous voids are formed on the surface of the concrete and the inside thereof so that a porous concrete is formed, with a larger surface area to be made in contact with water and an easy permeation of water being prepared; thus, the organism attractant substance is easily allowed to flow out into the environment from the entire concrete.

Moreover, when, by using the concrete of the present invention, a wave-absorbing block 1 is formed into a shape with a larger surface area, the amount of the flowing-out organism, attractant substance can be further increased.

In the present embodiment, in order to further increase the surface area of the wave-absorbing block 1, the respective four legs 2a, 2b, 2c and 2d are allowed to have plane portions 23, each formed between each pair of six ridge line portions 22 formed in the length direction of the respective legs 2a, 2b, 2c and 2d so that each leg is formed as a hexagonal prism having aright hexagonal shape in its cross section. Moreover, each of the legs 2a, 2b, 2c and 2d is formed into a hexagonal pyramid the area of the cross sectional shape of which is gradually narrowed toward the tip 3b from the base end portion 3a, and the end face 24 of the tip 3b is also cut to be a flat surface.

Moreover, of the four legs 2a, 2b, 2c and 2d, the base end portions 3a of the three legs (in FIG. 1, the legs 2a, 2b and 2c) are joined to one another at respective four portions, and each of the four portions has a virtually horizontal surface, and concave portions 5 are respectively formed on the center portions of the respective horizontal surfaces. Each of the concave portions 5 is formed by three first concave portions 5a that are formed in a discontinuously separated manner and one second concave portion 5b formed on an inner portion surrounded by the three first concave portions 5a.

Here, each of the first concave portions 5a is formed between mutually adjacent legs (in FIG. 1, between legs 2a and 2b, between legs 2b and 2c, as well as between legs 2c and 2a) of the three legs (in FIG. 1, legs 2a, 2b and 2c). Additionally, cut-out portions 6 respectively formed in the respective first concave portions 5a is used for easily discharging water entered the inside of each of the first concave portions 5a externally.

On the other hand, the second concave portion 5b is formed on an inside portion surrounded by the three first concave portions 5a, so as to have a rectangular shape on a plan view, with a step portion being formed on an inner side of the first concave portion 5a. Moreover, on the bottom surface 8 of the second concave portion 5b, fine striped irregularities, not shown, are formed.

The wave-absorbing blocks 1 having the structure as described above are arranged and placed side by side in water and along an embankment near a coast of a fishing harbor, a seashore, a river, etc., so as to form a fish reef or a wave-absorbing bank. Additionally, upon constructing a fish reef or a wave-absorbing bank, the wave-absorbing blocks 1 are not limited to a one-stage alignment, and may be arranged with several stages.

Thus, since the wave-absorbing blocks 1 placed in water maintain a large surface area of concrete made in contact with water, and since the organism attractant substance kneaded in the concrete is allowed to gradually ooze from the concrete surface in an appropriate amount portion by portion in a long period of time, the congregating and growing effects for fishes and shellfishes and the adhering and growing effects for algae can be maintained for a long period of time.

Furthermore, when used as a wave-absorbing bank, the concave portions 5 make it possible to alleviate the impact of waves. In this case, since the first concave portions (upper stage) 5a are formed near the outer surface of the block 1, water is hardly held therein; however, since the second concave portions (lower stage) 5b are formed in its recessed inner side in comparison with the first concave portions 5a, water is easily held therein, and spores of sea weeds, etc. are easily captured by the second concave portions 5b to form various living environments for algae, fishes, shellfishes and the like. Moreover, since the surface with striped fine irregularities is formed on the bottom surface 8, the surface with fine irregularities allows algae and shellfishes, such as abalone, to easily adhere thereto.

EXAMPLES

Strength Test for Concrete with Arginine Added Thereto

In order to test the strength of the environmentally active concrete of the present invention, concrete was adjusted to have compositions as shown in Table 1, and after having been poured into a frame of ϕ12.5×25, these were cured for 28 days. A strength test was carried out on the resultant test sample.

TABLE 1

| | Comparative Example 1 | Example 1 | Example 2 |
|---|---|---|---|
| Cement (kg/m$^3$) | 237 | ← | ← |
| Water (kg/m$^3$) | 149 | ← | ← |
| Fine aggregate (kg/m$^3$) | 877 | ← | ← |
| Coarse aggregate (kg/m$^3$) | 1207 | ← | ← |
| AE water-reducing agent (kg/m$^3$) | 1.185 | ← | ← |
| Arginine (kg/m$^3$) | 0 | 7.11 | 16.59 |
| Arginine addition ratio (%)*[1] | 0 | 3 | 7 |
| Compression strength (N/mm$^2$)*[2] | 18 | 25.4 | 22.9 |

*[1]Addition ratio relative to cement weight,
*[2]Nominal strength

As a result, it is clarified that even when 7% of arginine is added relative to the cement weight, the compression strength of the concrete is not lowered.

(Sensory Evaluation Test on Density and Odor of Concrete with Arginine Added Thereto)

Next, test samples having compositions as shown in Table 2 were prepared, and after having been poured into a frame of ϕ12.5×25, these were cured for 7 days. A density of each of the resultant test samples was examined. Table 2 shows the results thereof.

TABLE 2

| | Comparative Example 2 | Example 3 | Example 4 | Example 5 |
|---|---|---|---|---|
| Cement (kg/m$^3$) | 237 | ← | ← | ← |
| Water (kg/m$^3$) | 149 | ← | ← | ← |
| Fine aggregate (kg/m$^3$) | 877 | ← | ← | ← |
| Coarse aggregate (kg/m$^3$) | 1207 | ← | ← | ← |
| Mixing agent (kg/m$^3$) | 1.185 | ← | ← | ← |
| Arginine (kg/m$^3$) | 0 | 2.37 | 7.11 | 11.85 |
| Arginine addition ratio (%)*[1] | 0 | 1 | 3 | 5 |
| Slump (cm) | 6.0 | 16.5 | 20.0 | 21.5 |
| Amount of air (%) | 4.6 | 8.0 | 6.0 | 6.8 |
| Concrete density (g/cm$^3$) | 2.28 | 2.19 | 2.19 | 2.19 |

*[1]Addition ratio relative to cement weight

As a result, it is confirmed that those samples to which arginine was added had a smaller value in concrete density and tended to have higher values in amount of air and slump. This indicates that concrete to which arginine was added had a porous structure.

Next, sensory evaluation was carried out on test samples of comparative example 2 and examples 3, 4 and 5. The evaluation was conducted by seven panelists who examined odor generated by each of the test samples based upon Table 3. Table 4 shows the results thereof.

TABLE 3

| Definition | Points |
|---|---|
| No odor | 0 |
| Slight odor | 1 |
| Clear odor | 3 |

TABLE 4

| Panelists | Comparative Example 2 | Example 3 | Example 4 | Example 5 |
|---|---|---|---|---|
| A | 0 | 0 | 3 | 1 |
| B | 0 | 0 | 3 | 3 |
| C | 1 | 1 | 1 | 3 |
| D | 0 | 0 | 1 | 0 |
| E | 0 | 0 | 1 | 3 |
| F | 0 | 0 | 3 | 3 |
| G | 1 | 0 | 3 | 3 |
| Average | 0.3 | 0.1 | 2.1 | 2.3 |

As indicated by Table 4, significant odor of arginine was confirmed in test samples with an added amount of arginine of 3% or more relative to cement weight.

(Submerging Test in River)

Blocks having compositions of comparative example 2 and example 5 were prepared, and subjected to submerging tests in a river of Yamaguchi Prefecture. In the river, the reproductive state of sweetfish was mainly confirmed, and the reproductive state of algae on the block surface and the bite marks of sweetfish were visually observed.

Table 5 shows the results thereof.

TABLE 5

|  | Comparative Example 2 | | Example 5 | | Natural Rock | |
| --- | --- | --- | --- | --- | --- | --- |
|  | Bite Mark | Algae | Bite Mark | Algae | Bite Mark | Algae |
| 7/7 (Date of Submergence) | — | — | — | — | — | — |
| 8/6 | — | — | — | — | — | — |
| 8/20 | — | — | ++ | ++ | + | — |
| 9/4 | +‡ | + | +‡ | + | +‡ | + |
| 9/17 | +‡ | + | +‡ | + | +‡ | + |

*Presumed as old bite marks.

As a result, in the blocks to which arginine was added, significant attractant effects of sweetfish were confirmed based upon the bite marks of sweetfish and reproductive state of algae.

(Submerging Test in Sea)

Blocks having compositions of comparative example 2 and example 5 were prepared, and submerged in a harbor portion at a southern point of the Osaka Bay, and the reproductive state of algae was mainly observed visually. One month after the submergence, algae of the genus Ulva was inhabiting on the surface, and the inhabitant of algae on the concrete block having the composition of example 5 was significantly confirmed. The results thereof are shown in Table 6.

TABLE 6

|  | Comparative Example 2 | Example 5 |
| --- | --- | --- |
| One month later | ++ | +++ |
| Two months later | + | ++ |
| Three months later | + | ++ |

As the fact to be mentioned specifically, a large group of fish (*Girella punctata*) congregating on the periphery of the block was significantly observed with respect to the concrete block having the composition of example 5.

Additionally, it is needless to say that the invention is not limited to the above embodiments, but that various changes may be made within the scope not departing from the gist of the invention.

As described above, the present invention has been explained by exemplifying the case in which it is applied to wave-absorbing blocks; however, not limited to the wave-absorbing blocks, the present invention may be applied to general-use concrete blocks.

The invention claimed is:

1. An environmentally active concrete structure having cement, which is formed by kneading therein arginine that has congregating, adhering and growing effects for organisms, comprising:
    an environmentally active concrete structure containing the arginine at a concentration greater than three percent by weight relative to the cement so as to allow the arginine to effectively flow out gradually into a river, a seashore or the sea, as well as a pond or a lake for a period of time, with the resulting concrete structure being porous and having an attractant effect by odor of the flow-out arginine,
    said concrete structure has a shape comprising four legs extending radially from a center, each of said four legs having a hexagonal prism shape and a base adjacent to the center, three first concave portions formed adjacent to an outer surface of the shape and adjacent to and extending between the bases of two legs at a junction of three of the four legs, and a second concave portion formed at the center surrounded by the three first concave portions, said second concave portion being deeper than said first concave portion, whereby water is held within the second concave portion forming a living environment for the growth of organisms,
    wherein the environmentally active concrete structure is used for engineering constructions.

2. A method for congregating, adhering and/or growing organisms, comprising the steps of:
    forming the environmentally active concrete structure according to claim 1; and
    placing the concrete structure in water.

3. The method according to claim 2, wherein the method comprises congregating and growing fishes.

4. An environmentally active concrete structure for placing in water and promoting growth of organisms and attracting fish comprising:
    concrete having cement; and
    arginine mixed with said cement, said arginine having a percent by weight sufficient to increase the porosity of said concrete structure and create an odor of said arginine, and
    said concrete structure has a shape comprising four legs extending radially from a center, each of said four legs having a hexagonal prism shape and a base adjacent to the center, three first concave portions formed adjacent to an outer surface of the shape and adjacent to and extending between the bases of two legs at a junction of three of the four legs, and a second concave portion formed at the center surrounded by the three first concave portions, said second concave portion being deeper than said first concave portion, whereby water is held within the second concave portion forming a living environment for the growth of organisms.

5. A method of promoting growth of organisms and attracting fish comprising the steps of:
    forming the concrete structure according to claim 4; and
    placing the structure in water.

6. An environmentally active concrete structure for placing in water for promoting growth of organisms and attracting fish comprising:
    a concrete structure made from concrete having cement containing arginine at a concentration greater than three percent by weight relative to the cement; and
    said concrete structure comprising four legs extending radially from a center, each of said four legs having a hexagonal prism shape and a base adjacent to the center, three first concave portions adjacent to and extending between the bases of two legs at a junction of three of the four legs, and a second concave portion formed at the center surrounded by the three first concave portions, said second concave portion being deeper than said first concave portion, whereby water is held within the second concave portion forming a living environment for the growth of organisms and the arginine releases into the water from said concrete structure.

\* \* \* \* \*